United States Patent
O'Connor et al.

(10) Patent No.: US 6,634,213 B1
(45) Date of Patent: Oct. 21, 2003

(54) PERMEABLE PROTECTIVE COATING FOR A SINGLE-CHIP HYDROGEN SENSOR

(75) Inventors: James M. O'Connor, Ellicott City, MD (US); Thomas C. Loughran, Columbia, MD (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/788,977

(22) Filed: Feb. 20, 2001

Related U.S. Application Data

(60) Provisional application No. 60/183,642, filed on Feb. 18, 2000.

(51) Int. Cl.[7] .......................... H01L 7/00; G01N 27/16; G01N 27/00; B32B 9/00; H01C 1/02
(52) U.S. Cl. .................. 73/31.06; 73/31.05; 73/23.31; 340/634; 422/94; 436/144; 204/429; 204/415
(58) Field of Search .................. 73/31.06, 31.05, 73/23.2, 23.31; 422/94, 98; 340/634; 436/144; 204/424, 429, 415

(56) References Cited

U.S. PATENT DOCUMENTS

| | | | |
|---|---|---|---|
| 4,256,985 A | * | 3/1981 | Goodson et al. ............. 307/308 |
| 4,302,530 A | * | 11/1981 | Zemel ......................... 430/311 |
| 4,507,643 A | * | 3/1985 | Sunano et al. ................. 338/34 |
| 4,792,433 A | * | 12/1988 | Katsura et al. ................ 422/98 |
| 4,892,834 A | * | 1/1990 | Rauh .......................... 436/149 |
| 4,911,892 A | * | 3/1990 | Grace et al. .................. 422/94 |
| 4,977,658 A | | 12/1990 | Awano et al. ............... 29/25.01 |
| 5,279,795 A | | 1/1994 | Hughes et al. ................. 422/98 |
| 5,334,350 A | * | 8/1994 | Friese et al. ................... 422/98 |
| 5,367,283 A | | 11/1994 | Lauf et al. ..................... 338/34 |
| 5,493,897 A | | 2/1996 | Nomura et al. ............... 73/23.2 |
| 5,553,495 A | * | 9/1996 | Paukkunen et al. ....... 73/335.03 |
| 5,635,628 A | * | 6/1997 | Fleischer et al. ........... 73/31.06 |
| 5,668,301 A | | 9/1997 | Hunter ........................ 73/23.2 |
| 5,698,771 A | | 12/1997 | Shields et al. .............. 73/31.05 |
| 5,841,021 A | * | 11/1998 | De Castro et al. ............ 73/23.2 |
| 6,006,582 A | | 12/1999 | Bhandari et al. ............. 73/23.2 |
| 6,027,622 A | * | 2/2000 | Graser et al. ................ 204/426 |
| 6,041,643 A | | 3/2000 | Stokes et al. ............... 73/31.06 |
| 6,070,450 A | * | 6/2000 | Takao et al. ................ 73/31.05 |
| 6,101,865 A | * | 8/2000 | Meixner et al. ............ 73/23.32 |
| 6,114,943 A | | 9/2000 | Lauf ............................ 338/34 |
| 6,155,099 A | | 12/2000 | Kobayashi et al. ......... 73/31.05 |
| 6,182,500 B1 | | 2/2001 | Stokes et al. ............... 73/31.06 |

OTHER PUBLICATIONS

U.S. patent application Ser. No. 09/729,147, O'Connor, filed Dec. 1, 2000.

Stuart, Mark, "Using Hydrophobic Membranes to Protect Gas Sensors", Sensors, May 1998, at 14–20.

Cheng, Yang–Tse, et al., "Preparation and Characterization of Pd/Ni Thin Films for Hydrogen Sensing", in Sensors and Actuators B 30, 1996, at 11–15.

Hughes, R.C., et al., "Thin Films of Pd/Ni Alloys for Detection of High Hydrogen Concentrations", 71 J. Appl. Phys. 542, Jan. 1992, at 542–544.

Hughes, R.C. et al., "Thin Film Porous Membranes for Catalytic Sensors", in Digest of the 1997 International Conference on Solid State Sensors and Actuators, Transducers '97.

(List continued on next page.)

Primary Examiner—Hezron Williams
Assistant Examiner—J. David Wiggins
(74) Attorney, Agent, or Firm—McDonnell Boehnen Hulbert & Berghoff

(57) ABSTRACT

A permeable protective coating for a single-ship hydrogen sensor. A hydrogen-permeable coating is applied to a semiconductor wafer containing hydrogen sensor dies, prior to dicing of the wafer. The permeable coating is preferably an organic spin-on polymer, and the hydrogen sensors preferably include hydrogen-sensing elements composed of a palladium nickel alloy.

13 Claims, 9 Drawing Sheets

OTHER PUBLICATIONS

Author: Yang–Tse Cheng, Yang Li, Dan Lisi, W. M. Wang, Title: "Preparation And Characterization of Pd/Ni Thin films For Hydrogen Sensing", in the Sensors and Actuators B 30 (1996) 11–16, Article Received Sep. 5, 1994; revised Jan. 17, 1995; accepted Jan. 20, 1995, pp. 11–16.

Author: R. C. Hughes, W. K. Schubert, Title: "Thin Films Of Pd/Ni Alloys For Detection Of High Hydrogen Concentrations", in the J. Appl. Phys. 71 (1), Jan. 1, 1992, Received May 23, 1991, accepted for publication Sep. 27, 1991, pp. 542–544.

Author: R. C. Hughes, T. J. Boyle, T. J. Gardner, C. J. Brinker and Ross Thomas, Title: "Thin Film Porous Membranes For Catalytic Sensors", in the Digest of the 1997 International Conference on Solid State Sensors and Actuators, Transducers '97, pp.: All Pages.

Author: Mark Stuart, Pall Corp., Title: "Using Hydrophobic Membranes To Protect Gas Sensors" Sensors May 1998, All Pages.

* cited by examiner-

PERMEABLE PROTECTIVE COATING FOR A SINGLE-CHIP HYDROGEN SENSOR

PRIORITY

This application claims priority to and incorporates by reference U.S. Provisional Patent Application No. 60/183,642, titled "Permeable Protective Coating for Single-Chip Robust Hydrogen Sensor," filed on Feb. 18, 2000, and naming James M. O'Connor and Thomas C. Loughran as inventors.

FIELD

The present invention is related to hydrogen sensors, and more particularly, to a protective coating for a single-chip hydrogen sensor.

BACKGROUND

During the early 1990s, Sandia National Laboratory developed a single-chip hydrogen sensor that utilized Palladium-Nickel (PdNi) metal films as hydrogen gas sensors. U.S. Pat. No. 5,279,795. naming Robert C. Hughes and W. Kent Schubert as inventors, assigned to the United States as represented by the U.S. Department of Energy, describes such a sensor and is incorporated by reference herein. One of the key benefits of the sensor described in the '795 patent is its ability to detect a dynamic range of hydrogen concentrations over at least six orders of magnitude. Prior solutions to the problem of detecting hydrogen concentrations had been generally limited to detecting low concentrations of hydrogen. These solutions include such technologies as metal-insulator-semiconductor (MIS) or metal-oxide-semiconductor (MOS) capacitors and field-effect-transistors (FET), as well as palladium-gated diodes.

The hydrogen sensor described in the '795 patent was a notable advance in hydroponic-sensing technology. It was, however, primarily limited to an experimental laboratory environment due to the difficulties encountered in manufacturing such a sensor. Difficulties in producing such semiconductor devices due to the specialized materials used might result in low device production yields. An economically feasible commercial hydrogen sensor is difficult to obtain if yields are under an acceptable level.

The assignee of the present invention has developed techniques to improve device yields in an attempt to manufacture a commercializable single-chip hydrogen sensor. Two of these techniques are described respectively in U.S. patent application Ser. No. 09/729,147, titled "Robust Single-Chip Hydrogen Sensor," filed Dec. 1, 2000, and U.S. patent application Ser. No. 09/878,668, titled "Manufacturable Single-Chip Hydrogen Sensor," filed concurrently herewith, both of which are incorporated by reference herein.

These improved sensors are still, however, prone to possible yield problems. A major source of yield problems arises from the poor adhesion of the hydrogen sensing material (typically a PdNi thin film) to the underlying chip structure. As a result, although the PdNi films may survive processing and initial testing, many of the PdNi structures are lost during subsequent wafer dicing. Wafer dicing is practically a requirement to producing a commercializable hydrogen sensor, due to the efficiencies that arise from mass producing sensors on a single wafer.

Initial attempts have involved depositing a protective coating, such as photoresist, over the wafer, prior to dicing. Although this technique shows some promise in preventing the loss of PdNi, the yield has not substantially improved. Moreover, the protective layer must be removed before the chip can sense hydrogen. Such a removal operation can lead to further yield losses.

In addition to protecting sensing elements during wafer dicing, there is also a need to provide protection from hazards that might be encountered in the sensing environment. For example, a durable coating might be desired to protect the sensing elements from physical damage, such as scratches. Also, the particular testing environment might contain chemicals that might be harmful to an unprotected sensor chip. For example, an environment that contains hydrochloric acid might damage the sensing elements on an unprotected sensor.

To protect against environmental hazards, individual sensors have recently been covered With a permeable membrane that allows a gas to pass through while providing some degree of protection for the sensor. See, for example, Stuart, M., "Using Hydrophobic Membranes to Protect Gas Sensors," Sensors, p. 14, May 1998. Such a technique, however, does not protect the on-chip components during wafer dicing and/or assembly, because the membrane is applied after processing and wafer dicing.

Thus, it would be desirable to provide a protective coating for a single-chip hydrogen sensor that is capable of providing protection during the manufacture of the sensor, and that allows hydrogen levels to be sensed while the protective coating is in place.

It would also be desirable to provide a robust single-chip hydrogen sensor that is capable of sensing hydrogen concentrations over a broad range, such as from approximately 1% to approximately 100% concentrations.

It would also be desirable for such a sensor to be efficiently manufacturable, so that costs are reduced and the sensor is producible in high enough yields to enable commercialization.

It would be desirable for such a sensor to provide measurement results that approximate or improve on the results from previous hydrogen sensors.

It would additionally be desirable to minimize sensor drift and to improve device-to-device and wafer-to-wafer repeatability.

SUMMARY

In accordance with an illustrative embodiment of the present invention, some of the problems associated with manufacturing a robust hydrogen sensor are addressed.

In a first aspect of the invention, a semiconductor wafer including a plurality of hydrogen sensors is provided. The wafer includes a hydrogen-permeable coating disposed over the plurality of hydrogen sensors. The plurality of hydrogen sensors may each include one or more sensing elements, such as palladium nickel sense resistors or transistors. In a further embodiment, the semiconductor wafer further includes at least one temperature sensor for determining a sensor temperature and at least one temperature controller for controlling the temperature of the sensor. The hydrogen-permeable coating is preferably an organic spin-on polymer.

In a second aspect of the invention, a robust hydrogen sensor is provided. The sensor includes a silicon base portion, at least one hydrogen-sensing element disposed on the silicon base portion, and a hydrogen-permeable coating disposed over the at least one hydrogen-sensing element. The sensor may, for example, include at least one palladium nickel sense resistor for determining hydrogen concentration within a first range and at least one palladium nickel sense transistor for determining hydrogen concentration within a second range. The hydrogen-permeable coating is preferably an organic spin-on polymer.

In a third aspect, a method for fabricating a robust single-chip hydrogen sensor is provided. The method includes providing a plurality of hydrogen sensors on a wafer, applying a hydrogen-permeable coating to the wafer, and separating the wafer into a plurality of dies. The method may further include providing a temperature sensor and a temperature controller on the wafer. The hydrogen-permeable coating may, for example, be an organic polymer.

In a fourth aspect, a method for fabricating a robust single-chip hydrogen sensor is provided. The method includes applying a hydrogen-permeable coating over at least one hydrogen-sensing element disposed on a wafer. For example, the hydrogen-sensing element may include at least one palladium nickel sense resistor for determining hydrogen concentration within a first range and at least one palladium nickel sense transistor for determining hydrogen concentration within a second range. The hydrogen-permeable coating is preferably an organic spin-on polymer, which may be applied by securing the wafer on a chuck, rotating the chuck, thereby rotating the wafer, and dripping, the hydrogen-permeable coating onto the wafer. Other application processes, such as spray-coating, dip-coating, physical deposition, chemical vapor deposition, evaporation, and sputtering, may also be used.

BRIEF DESCRIPTION OF THE DRAWINGS

Presently preferred embodiments of the invention are described below in conjunction with the appended drawing figures, wherein like reference numerals refer to like elements in the various figures, and wherein.

DETAILED DESCRIPTION

Figure 1:
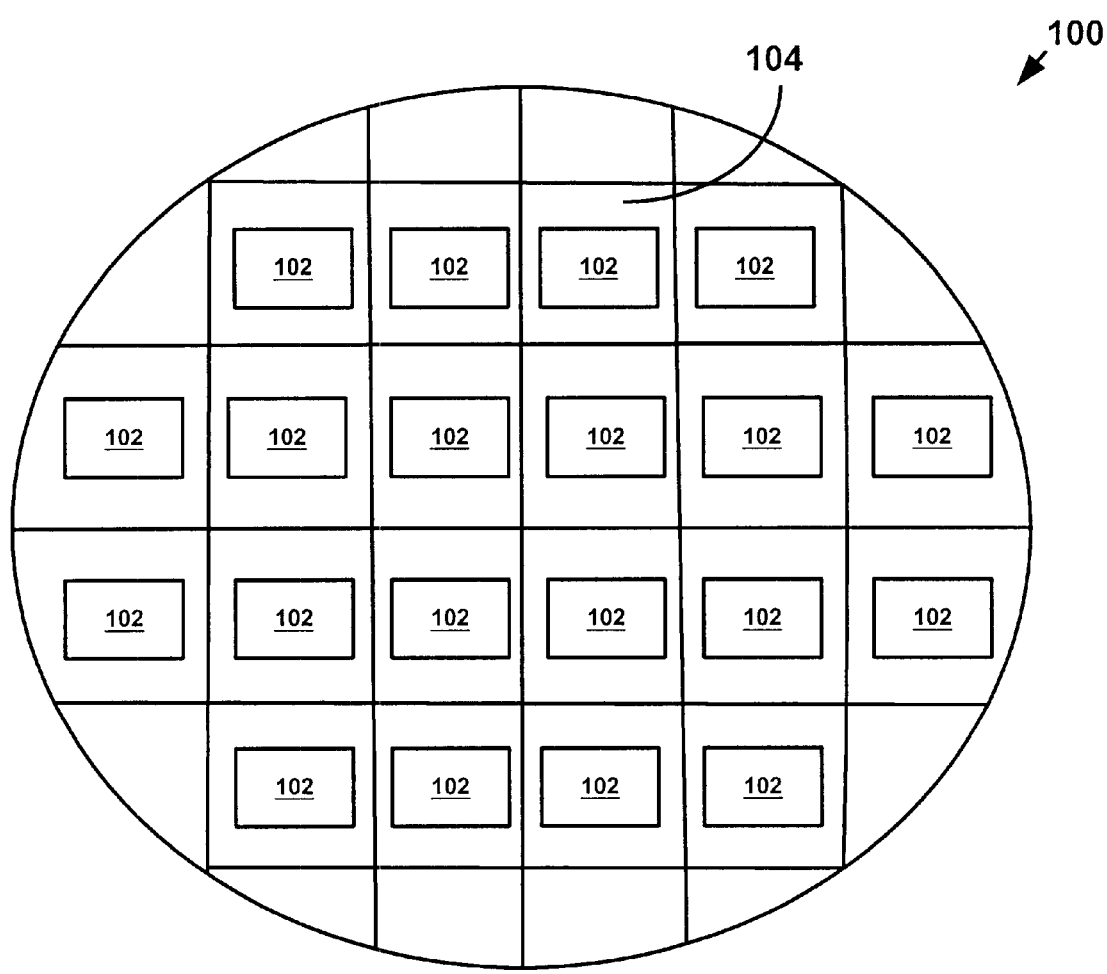
FIG. 1 is a simplified block diagram illustrating an exemplary semiconductor wafer having a plurality of hydrogen sensors.

FIG. 1 is a simplified block diagram illustrating an exemplary semiconductor wafer 100 having a plurality of hydrogen sensors 102. The wafer 100 may be separated into a plurality of dies 104. In the example shown in FIG. 1, each die 104 contains one hydrogen sensor 102. According to the present invention, a hydrogen-permeable coating (not shown) is disposed over the surface of the wafer 100 prior to separating the wafer 100 into the plurality of dies 104.

Figure 2A:
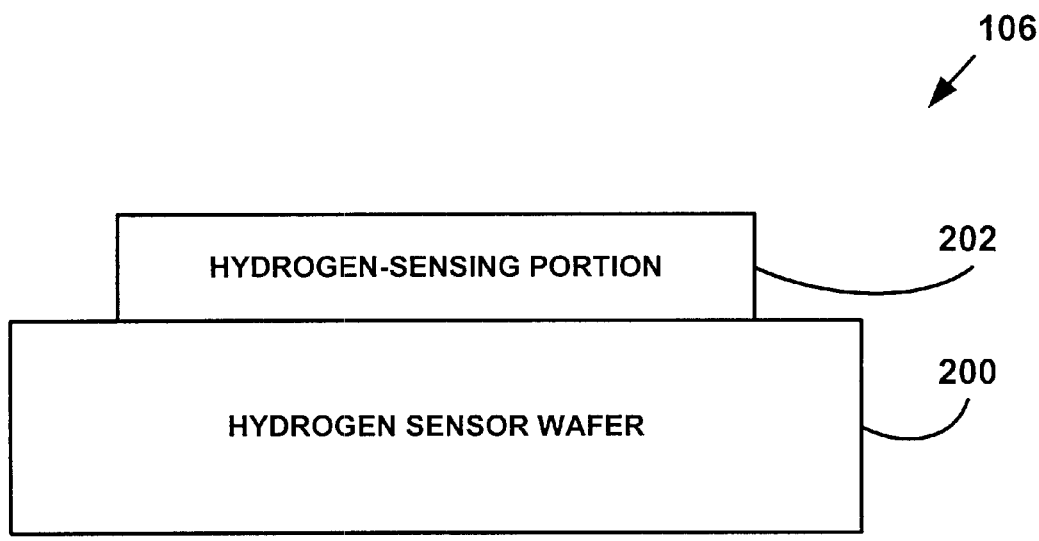
FIG. 2A is a simplified block diagram illustrating a typical semiconductor hydrogen sensor.

FIG. 2A is a simplified block diagram illustrating a typical semiconductor hydrogen sensor 106. A hydrogen-sensing portion 202 is disposed on a wafer 200. Because the hydrogen-sensing portion is exposed to the environment, it may be used to sense hydrogen concentrations. The hydrogen-sensing portion may, for example, be a PdNi film, for example. Its exposure to the environment, however, also subjects it to physical damage, such as scratches. Moreover, the hydrogen-sensing portion (or other portions) may be damaged during separation of the wafer into the individual dies. Other portions and/or components may also be included and are not shown in FIG. 2A.

Figure 2B:
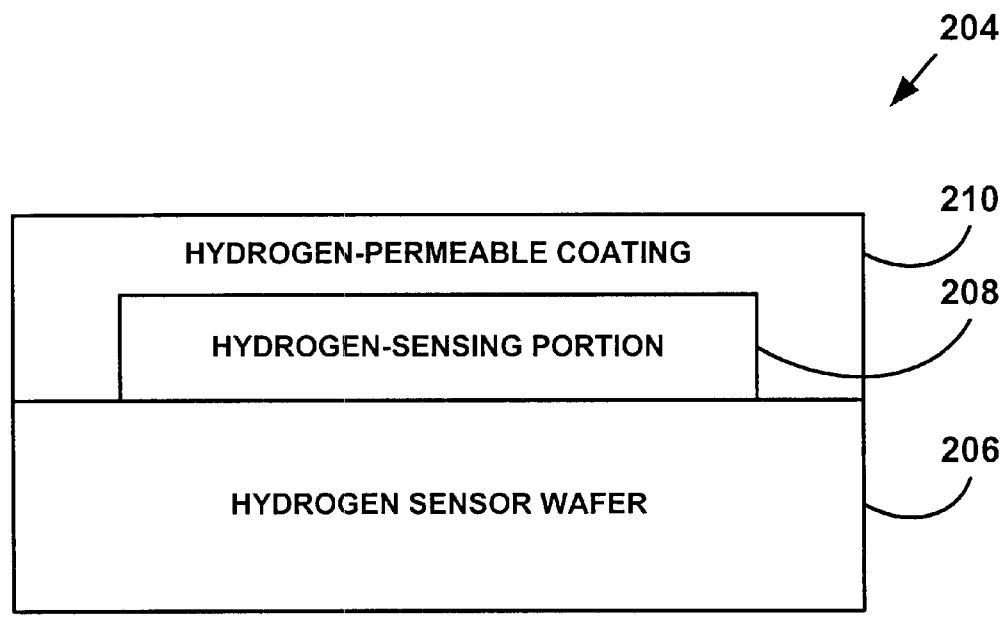
FIG. 2B is a simplified block diagram illustrating a hydrogen sensor according to an exemplary embodiment of the present invention.

FIG. 2B is a simplified block diagram illustrating a hydrogen sensor 204, according to an exemplary embodiment of the present invention. The sensor 204 includes a wafer 206 to serve as al base portion. A hydrogen-sensing portion 208 is disposed on the wafer 206. A hydrogen-permeable coating 210 is disposed over the hydrogen-sensing portion 208.

The hydrogen-sensing portion 208 may, for example, be a hydrogen-sensing element such as a sense resistor, a sense transistor, or a sense capacitor. In addition, more than one hydrogen-sensing element may be included in the sensor 204. In the preferred embodiment, the hydrogen-sensing portion 208 includes at least one PdNi sense resistor for determining hydrogen concentration within a first range, and at least one PdNi sense transistor for determining hydrogen concentration within a second range.

The hydrogen-permeable coating is preferably an organic polymer, such as an organic spin-on polymer. Other methods of coatings, such as a spray coating or a dip coating, may also be used. Additionally, other methods and materials for providing a hydrogen-permeable coating may also be used, such as physical or chemical vapor deposition, or sputtering. Because the hydrogen-permeable coating allows hydrogen to pass through, the hydrogen-sensing portion is able to detect a concentration of hydrogen in the environment in which the sensor 204 is situated. Further details regarding preferred coating materials are provided below, with reference to FIGS. 5A–6B.

Figure 3:
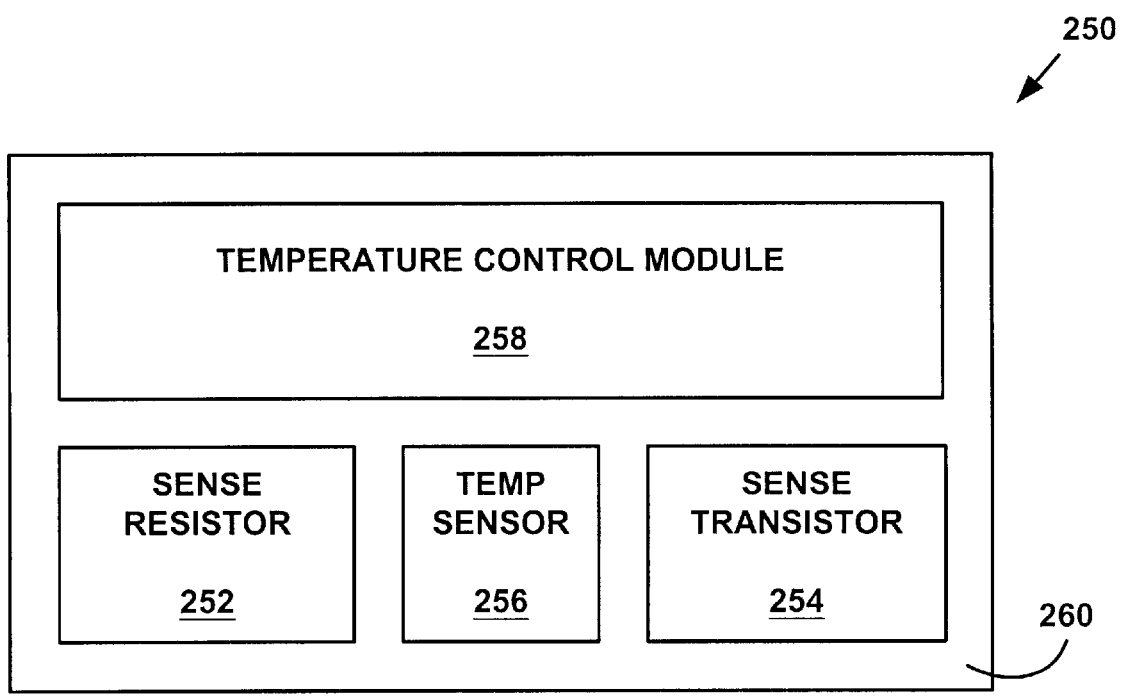
FIG. 3 is a simplified block diagram illustrating a top view of a robust single-chip hydrogen sensor in accordance with an embodiment of the present invention.

FIG. 3 is a simplified block diagram illustrating a top view of a robust single-chip hydrogen sensor in accordance with an embodiment of the present invention. The sensor 250 includes at least one sense resistor 252, at least one sense transistor 254, at least one temperature sensor 256, and at least one temperature control module 258 located in or on a substrate 260. On-chip and/or external circuitry (not shown) may be included to assist in precisely regulating, the temperature of the chip 250 using the temperature sensor 256 and the temperature control module 258. Similarly, the same external circuitry, or other external circuitry, may be used to obtain outputs from the sense resistor 252 and/or the sense transistor 254. A hydrogen-permeable coating (not shown) is disposed over at least a portion of the sensor 250, and may be disposed over the entire surface of the sensor 250.

The substrate 260 preferably is a bulk silicon substrate. Silicon enables the use of many common silicon semiconductor processing techniques, such as masks, implants, etchings, dopings, and others.

The temperature control module 258 preferably includes one or more heater Field-Effect-Transistors (FETs) or other heating devices (for example, resistive heating elements) formed in or on the substrate 260. One or more cooling mechanisms may additionally or alternatively be included as part of the temperature control module 258. The temperature control module 258 adjusts the temperature of the sensor 250 in response to temperature measurements received from the temperature sensor 256 or associated external circuitry.

The temperature sensor 256 is preferably a temperature sensing diode formed in or on the substrate 260. Other methods for sensing temperature may also be used.

The sense transistor 254 is used to sense hydrogen concentration levels in an environment in which the sensor 250 is placed. The sense transistor 254 is preferably a PdNi-gate sense transistor that is fabricated in or on the substrate 260. Other types of sense transistors may also be used. The sense transistor 254 may utilize Metal-Oxide-Semiconductor (MOS) or Metal-insulator-Semiconductor (MIS) technology. In an alternative embodiment, the sense transistor 254 may instead be a sensing element, such as a sense capacitor. (In such a case, alternating current measurement techniques may need to be employed.) The sense transistor 254 senses hydrogen concentration levels ranging from a first minimum concentration to a first maximum concentration. Typical values for the first minimum concentration and first maximum concentration are one part per million (ppm) and 1,000, ppm, respectively. Other minimum and maximum concentrations may also be possible for the sense transistor 254.

The sense resistor 252 is preferably a PdNi film arrayed in a serpentine pattern fabricated in or on the sensor 250. Other materials besides PdNi may be used, such as various palladium silicides and polymeric sensing elements. The resistance of the sense resistor 252 changes in the presence of hydrogen, enabling detection of hydrogen concentration in a particular environment. The sense resistor 252 is preferably operable to sense hydrogen levels ranging from a second minimum concentration to a second maximum concentration. Exemplar values for the second minimum concentration and lo second maximum concentration are 100 ppm and 1,000,000 ppm, respectively. Other minimums and maximums may also be possible.

Figure 4:
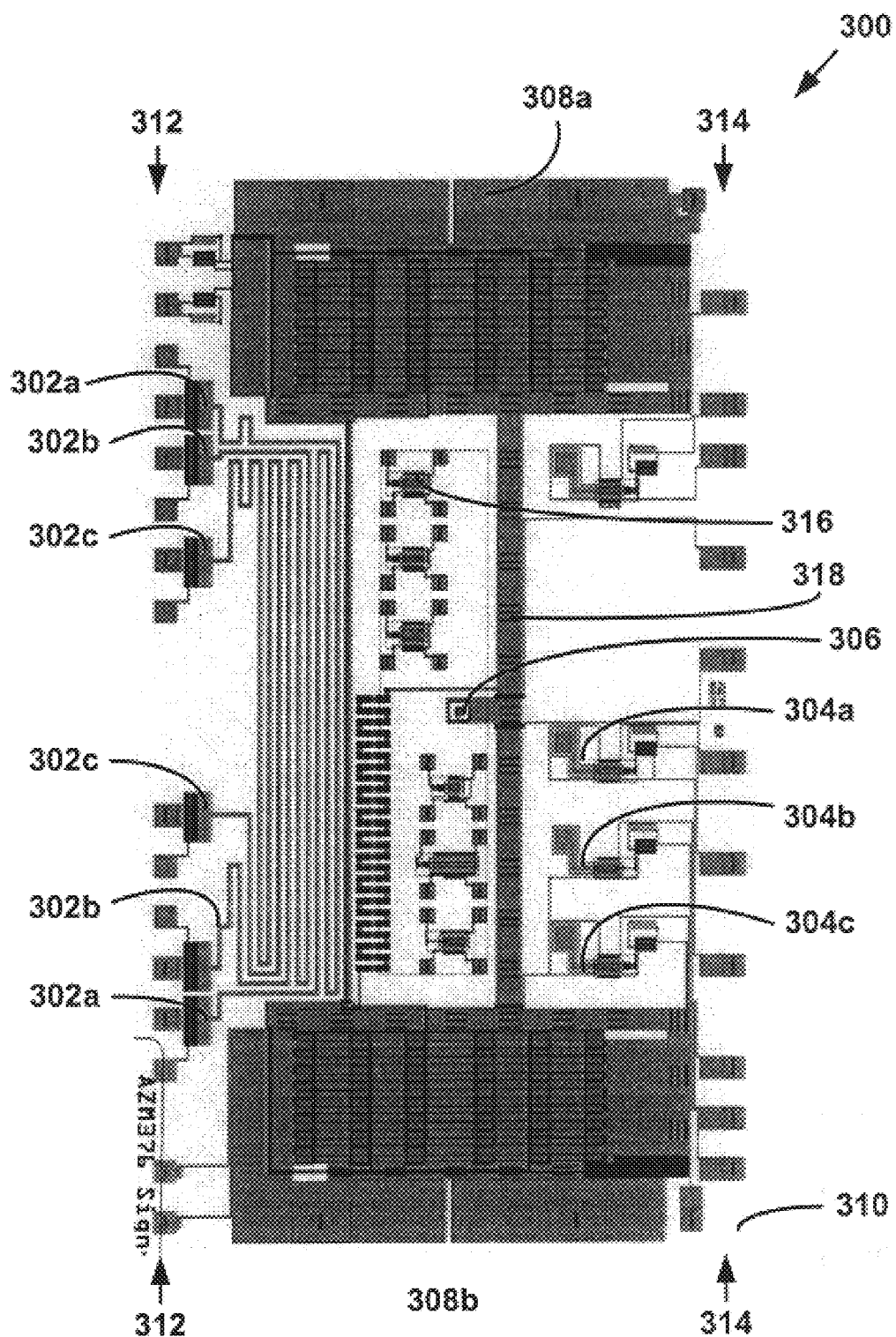
FIG. 4 is a block diagram illustrating a top view of a single-chip hydrogen-sensing device, according to a preferred embodiment of the present invention.

For purposes of illustration (lend to maintain generality, no connections arc shown, and no external circuitry is shown in FIG. 3. Connections are likely to exist between the resistor 252, the sense transistor 254, the temperature sensor 256, the temperature control module 258, and/or any external circuitry. Such connections may be made by a network of interconnect metallizations, for example. Further details on preferred connection layouts are shown in FIG. 4, described in further detail below.

Also not shown in FIG. 3 is all underlying, non-conductive layer that may be used to isolate the sense resistor 252, the sense transistor 254, the temperature sensor 256, and/or the temperature control module 258 from the substrate 260. The non-conductive layer may, for example, be a silicon nitride or oxide layer. As used throughout this description, the term "non-conductive" is intended to describe conductive characteristics when compared to a conductive material, such as aluminum, or a semiconductive material, such as silicon. "Non-conductive" is not intended to imply an actual inability to conduct electricity regardless of applied conditions. Also, as used herein, the term "interconnect metallization" will typically refer to a material that is conductive with respect to any non-conductive layers.

The hydrogen-permeable coating (not shown) is disposed over at least a portion, such as over the sense resistor 252 and sense transistor 254, of the sensor 250. Preferably, the hydrogen-permeable coating is disposed over the entire surface of the sensor. The hydrogen-permeable coating is applied during the processing of the sensor 250, so that an entire wafer surface is coated with the hydrogen-permeable coating. Various mask and etch procedures may be employed if complete coverage is not desired. The hydrogen-permeable coating is preferably an organic polymer coating, such as a spill-oil coating. Further details regarding the hydrogen-permeable coating may be found with reference to the description accompanying FIGS. 5A–6B.

Operation of the sensor 250 will now be described. The temperature sensor 256 and temperature control module 258 are used to regulate the operating temperature of the sensor 250 when sensing hydrogen. Tile temperature of the sensor 250 may, for example, be held at a constant sense temperature. The temperature sensor 256 and temperature control module 258 may also be used to purge hydrogen and/or other gases, etc. after measurements are taken, by heating the chip to a purge temperature. In the preferred embodiment, the temperature control module 258 heats the chip to approximately 80 degrees Celsius, as measured at the temperature sensor 256. The purge temperature is preferably approximately 100 degrees Celsius. One or more feedback loops may be used to assist in accurately regulating the temperature using the temperature sensor 256 and the temperature control module 258. Such feedback loop(s) may be included in external circuitry, for example. When the sensor 250 is in a hydrogen-sensing mode, then the sense resistor 252 and the sense transistor 254 preferably sense hydrogen levels at overlapping ranges. This enables the combination of the sense resistor 252 and the sense transistor 254 to provide measurements of hydrogen concentration over a larger range than a single sense element might otherwise provide. The determination as to when to purge may be made by examining, measurement outputs from the sense resistor 252 and/or the sense transistor 254. In the case of the sense resistor 252, the measurement output may be a particular resistance corresponding to the concentration of hydrogen gas in the environment of the sensor 250. Such a determination may be made by external circuitry and may be used to control the temperature control module 258.

FIG. 4 is a block diagram illustrating a top view of a single-chip hydrogen-sensing device 300, according to a preferred embodiment of the present invention. The device 300 includes a first sense resistor 302a, a second sense resistor 302b, and a third sense resistor 302c, to sense hydrogen concentrations at approximate first minimum concentrations and approximate first maximum concentrations. A first sense transistor 304a, a second sense transistor 304b, and a third sense transistor 304c may be used to sense hydrogen levels at second minimum concentrations and second maximum concentrations.

A temperature sensing diode 306 is used to determine the temperature of the device 300. A first heater Field Effect Transistor (FET) 308a and a second heater FET 308b are used to control the temperature of the device 300, so that the approximate temperature is 80 degrees Celsius during a hydrogen-sensing period and approximately 100 degrees Celsius during a purge period. The temperature sensing diode 306 and the heater FETs 308a–b are used in conjunction with external circuitry (not shown) to provide temperature regulation. A hydrogen-permeable coating is disposed over at least a portion of the sensor 300, and may be disposed over the entire surface of the sensor 300.

The sense resistors 302a–c, the sense transistors 304a–c, the temperature sensing diode 306, and the heater FETs 308a–b are located in and/or on a bulk semiconductor substrate 310. Additional layers may be present on the substrate 310, and are not shown in FIG. 2. For example, conductive and/or non-conductive layers may be deposited on one or more portions of the substrate 310. A series of left-side contacts 312 extend generally down the left side of the device and may be used to provide power, to receive measurements, and/or to control device operation. Similarly, right-side contacts 314 may be used to provide these same operations. In addition, the left-side contacts 312 and the right-side contacts 314 may be used for other functions, such as for testing the device 300. Special test elements, such as the test element 316 (and others resembling test element 316), may be located in or on the device 300 to enable verification that the device 300 is operating properly. An interconnection network 318 connects various components within the device 300. Most of the unreferenced components shown in FIG. 2 are test elements and/or interconnections between various referenced and unreferenced components.

The device 300 includes multiple sense resistors 302a–c, sense transistors 304a–c, and heater FETs 308a–b in order to provide redundancy. This enables the device 300 to operate in case one of the sensing mechanisms fails, and also enables improved accuracy due to more than one sensing element providing measurements and the ability to cross-check measurements. Other quantities of components within the device 300 may also be used without departing from the scope of the present invention.

The sense resistors 302a–c and the gates of the sense transistors 304a–c preferably include all alloy that resists the formation of a hydride phase of a catalytic metal contained in the alloy. The preferred alloy is a nickel and palladium alloy (PdNi). For example, an alloy of about 8% to 20% (by atom percentage) nickel (with the balance being palladium) may be used. Other alloy compositions and/or materials may also be used.

The hydrogen-permeable coating (not shown) is disposed over at least a portion, such as over the sense resistors 301a–c and sense transistors 304a–c, of the sensor 300. Preferably, the hydrogen-permeable coating is disposed over the entire surface of the sensor. The hydrogen-permeable coating is applied during the processing of the sensor 300, so that an entire wafer surface is coated with the hydrogen-permeable coating. Various mask and etch procedures may be employed if complete coverage is not desired. The hydrogen-permeable coating is preferably an organic polymer coating, such as a spin-oil coating,. Further details regarding the hydrogen-permeable coating may be found with reference to the description accompanying FIGS. 5A–6B.

TABLE 1 illustrates process steps that may be used to produce a single-chip hydrogen sensor that may be utilized in a preferred embodiment of the present invention. The steps arc preferably performed in order, from top-to-bottom, starting with the left column. The abbreviations correspond primarily to semiconductor processing steps. Such abbreviations should be readily apparent to those having skill in the relevant technology field. It should be noted that the application of a hydrogen-permeable coating is preferably applied at or near the end of the process shown in Table 1, prior to separation of the wafer into individual dies.

TABLE 1

| 5 | Phos. Implant | 25 | p+ mask | 45 | NiPd dep |
|---|---|---|---|---|---|
|   | initial ox |   | p+ implant |   | Acetone lift-off |
|   | diff mask |   | BF2 implant |   | Anneal |
|   | diff etch |   | h-gate mask |   |   |
|   | p-well mask |   | h-gate implant split |   |   |

TABLE 1-continued

| 10 | p-well imp | 30 | boe etchback |
|---|---|---|---|
|   | chan-stop imp |   | h-gate oxidation 200A |
|   | p-well drive |   | R&D nitride dep 200A |
|   | nitride strip |   | nitride 2 mask |
|   | threshold imp |   | nitride dry etch |
| 15 | gate ox | 35 | BPSG |
|   | poly dep |   | BPSG reflow |
|   | poly dope |   | contact mask |
|   | poly mask |   | contact etch |
|   | poly etch |   | metal 1 dep |
| 20 | spacer ox | 40 | metal 1 mask |
|   | n+ mask |   | metal 1 etch |
|   | n+ imp |   | Alloy |
|   | s/d implant |   | Lift-off mask |
|   | poly re-ox |   | Lift-off etch |

The process steps shown in Table 1 are exemplary only, and other processes and/or materials may be used. For example, the last few steps may be modified to utilize techniques described in U.S. patent application Ser. No. 09/729,147, titled "Robust Single-Chip Hydrogen Sensor," filed Dec. 1, 2000, and U.S. patent application Ser. No. 09/878,668, titled "Manufacturable Single-Chip Hydrogen Sensor," filed concurrently herewith.

Figure 5A:
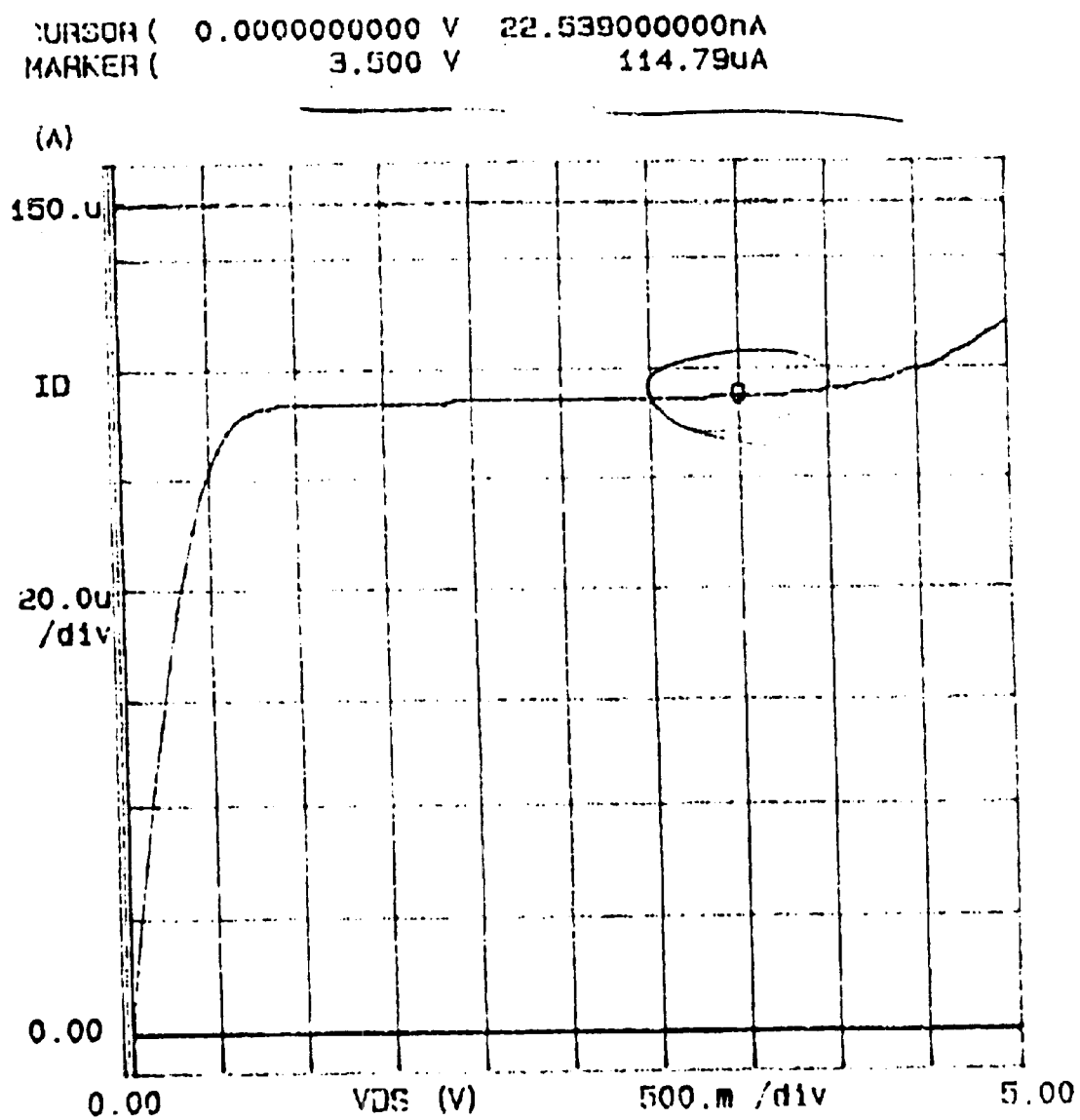
FIGS. 5A and 5B are traces illustrating sensor response when a first hydrogen-permeable coating is used.
Figure 5B:
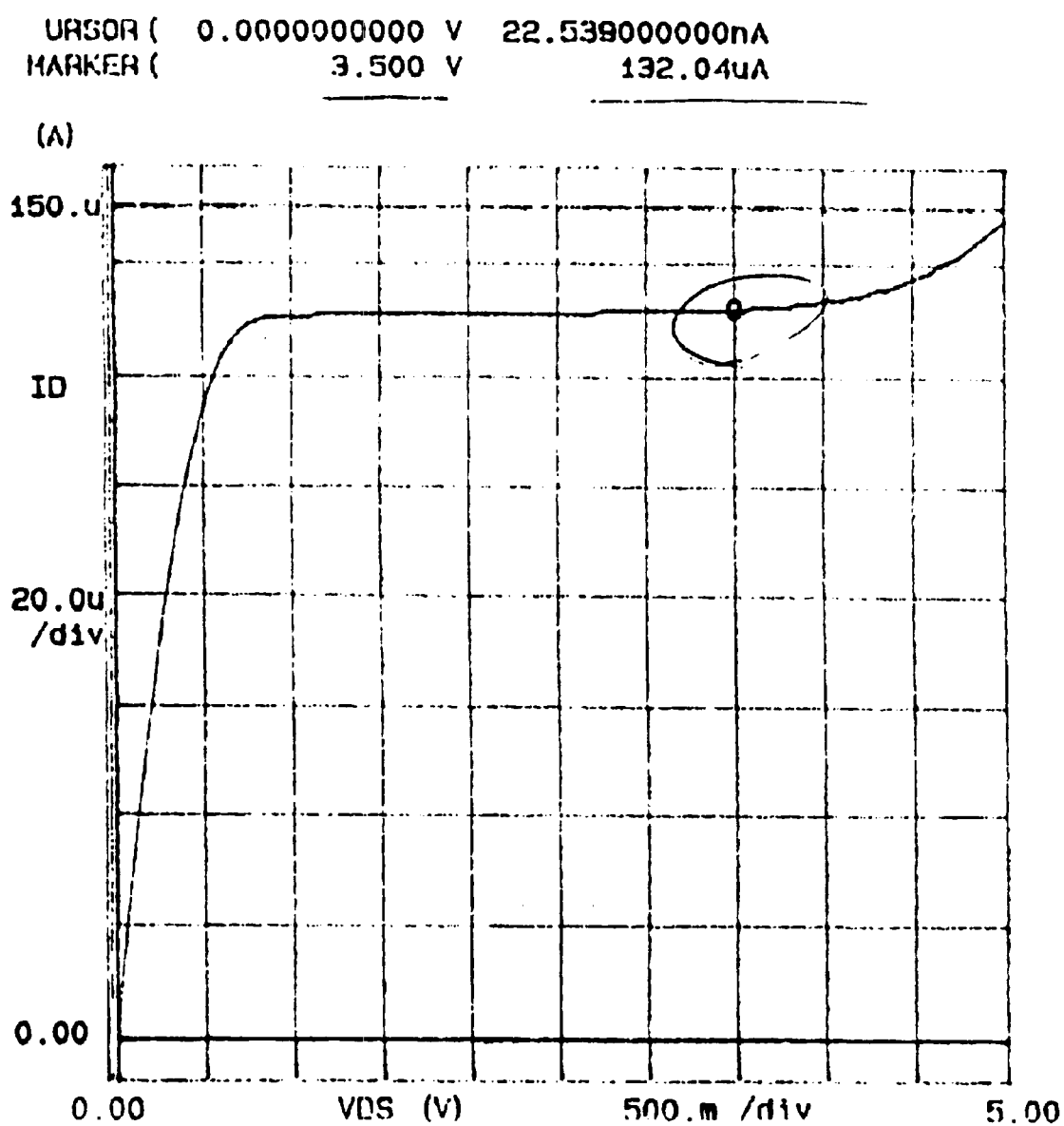
Figure 6A:
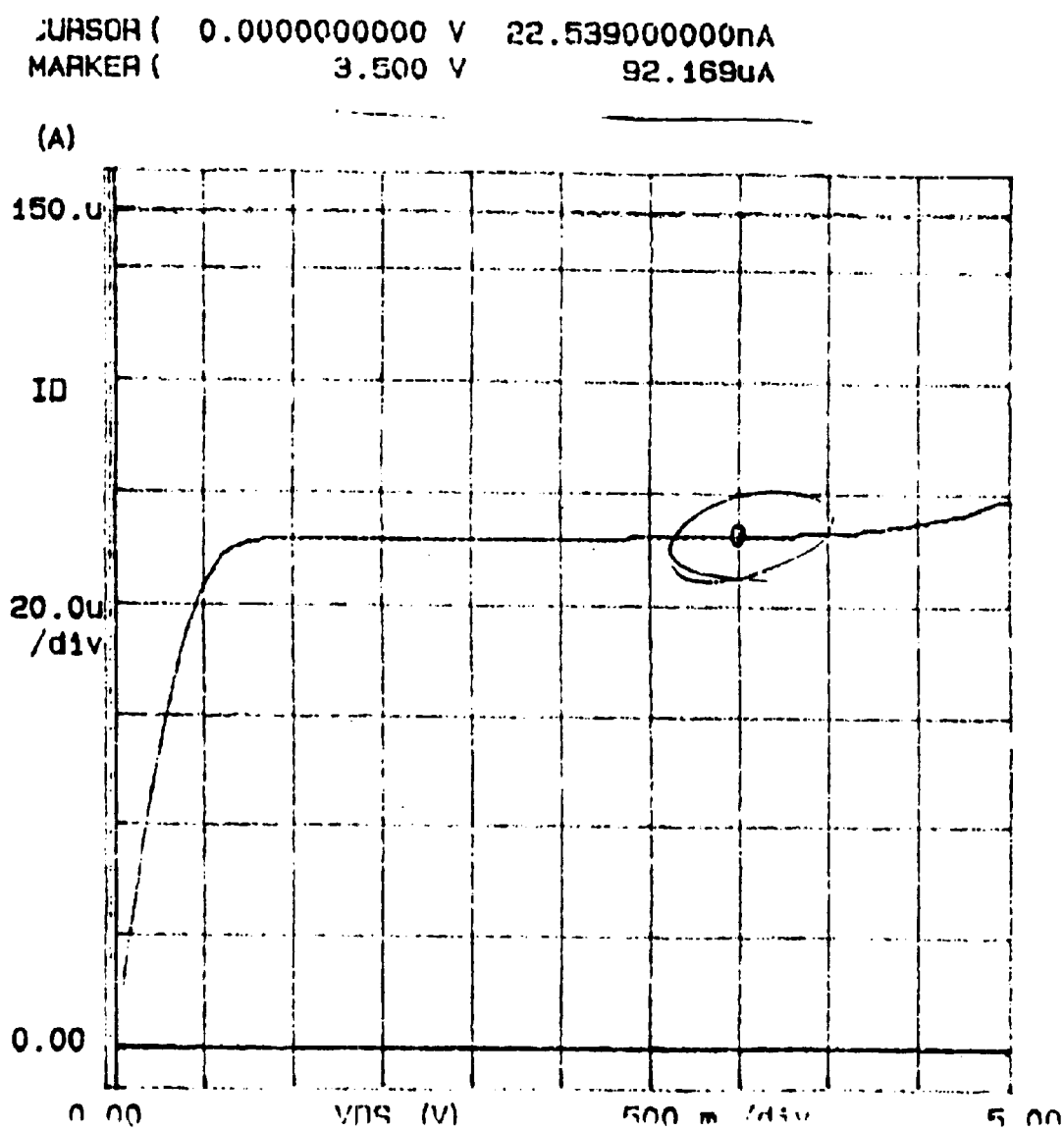
FIGS. 6A and 6B are are traces illustrating sensor response when a second hydrogen-permeable coating is used.
Figure 6B:
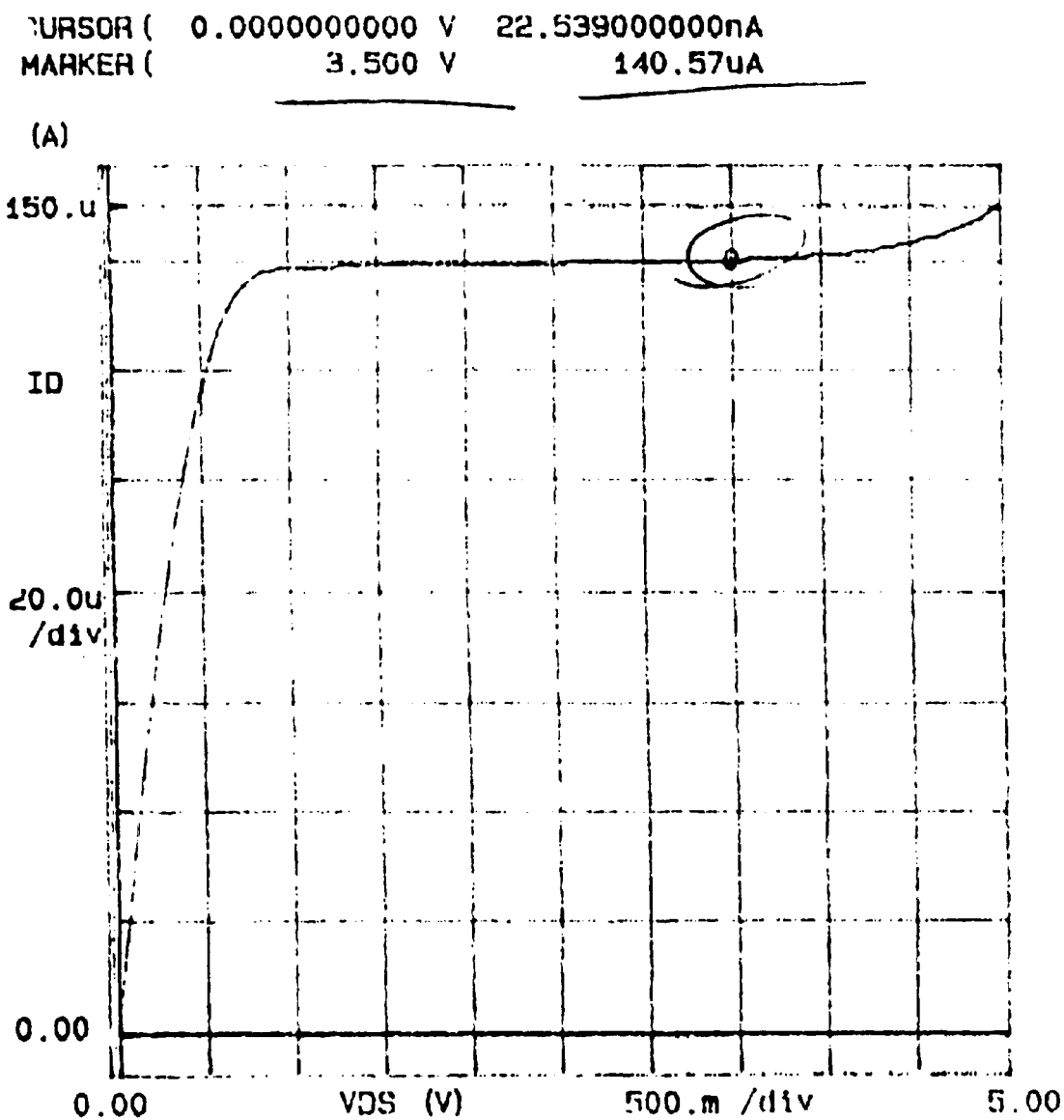

FIGS. 5A–B and 6A–B are exemplary test traces in which two sample wafers were coated with two different hydrogen-sensitive protective coatings. In FIGS. 5A and 5B, the water was coated with the FLARE™ organic spin-on polymer, available from the Advanced Microelectronic Materials division of Honeywell International Inc., located in Sunnyvale, Calif. Further details regarding the FLARE ™ coating may be found in the FLARE ™ Product Bulletin, February 1999, available at http://www.electronicmaterials.com as of the filing of this application, and incorporated by reference herein. In FIGS. 6A and 6B, the wafer was coated with the HOSP™ spin-on hybrid siloxane-organic polymer, also available from the Advanced Microelectronic Materials division of Honeywell International Inc. The spin-coating process included placing the wafer on a chuck, rotating the chuck (and wafer) at a high speed, and placing a few drops of the coating material on the wafer. The drops spread out over the surface of the wafer.

After each wafer was processed and annealed, sensors on each wafer were tested both in air and after a squirt of forming gas (<10% hydrogen in nitrogen). The sense transistors were both biased at $V_{GS}$=3.5 V. FIGS. 5A and 5B show the response of the wafer halving the FLARE ™ coating, in air and forming gas, respectively. As can be seen from comparing FIGS. 5A and 5B, there is a shift of 17 $\mu A$ in the presence of hydrogen, a percentage change of more than 14%. FIGS. 6A and 6B show the response of the wafer having, the HOSP ™ coating, in air and forming gas, respectively. As can be seen from comparing FIGS. 6A and 6B, there is a shift of 48 $\mu A$, a percentage change of more than 50%. Although these results are experimental only, and should not be used for quantitative analysis, they clearly show that the coatings pass hydrogen to the sensing elements present on the wafer. As a result, the ability to sense hydrogen is maintained, even though a protective coating overlies the sensing elements.

Although spin-coating was the process used to apply the hydrogen-permeable coatings used in the tests of FIGS. 5A–6B, other processes and coatings may also be used. For example, other known coating techniques, such as spray-coating, dip-coating, physical or chemical vapor deposition, evaporation, or sputtering, may be employed.

Figure 7:
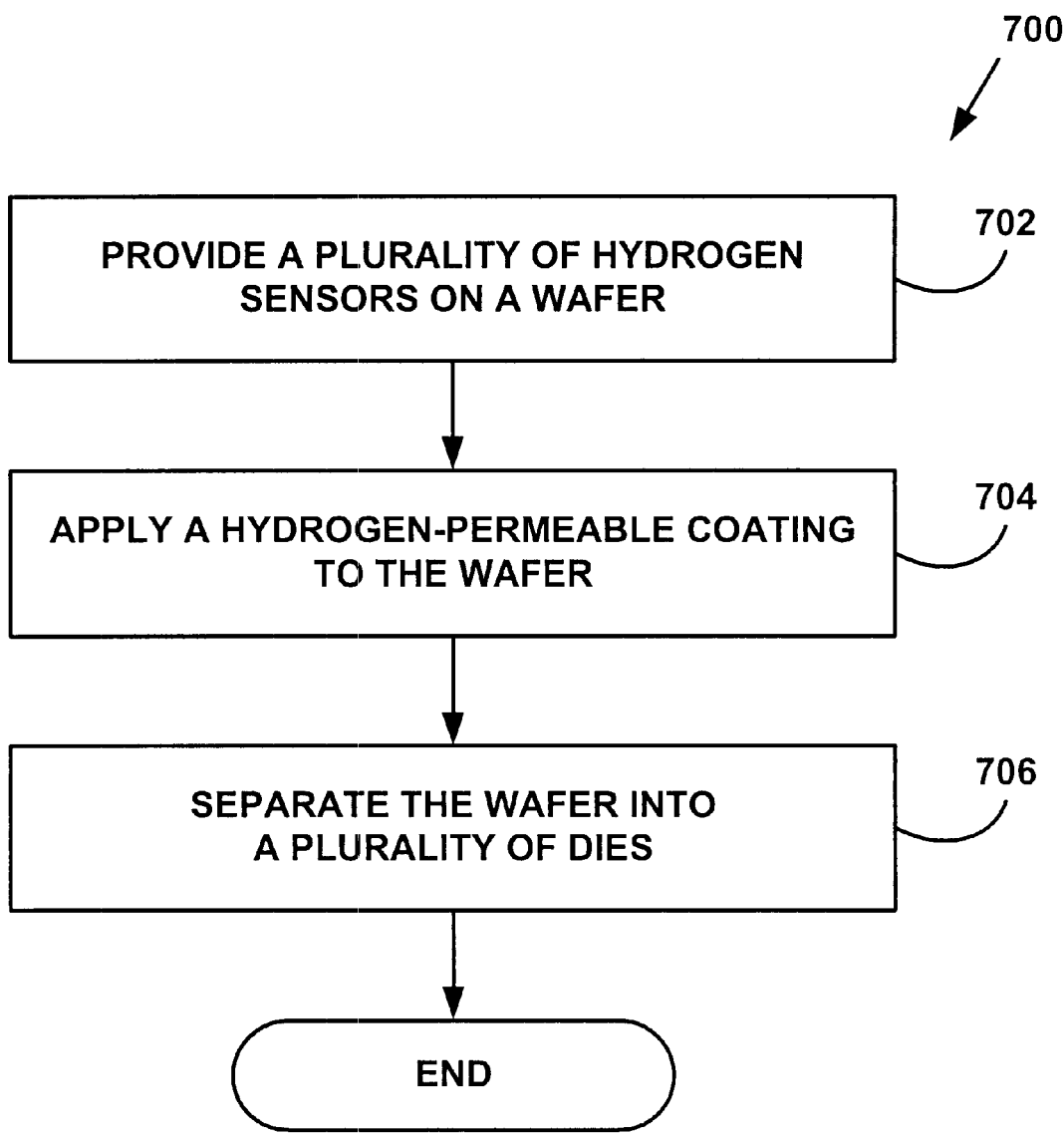
FIG. 7 is a flow diagram illustrating a method for fabricating a robust single-chip hydrogen sensor, according to a preferred embodiment of the present invention.

FIG. 7 is a flow diagram illustrating, a method 700 for fabricating a robust single-chip hydrogen sensor. A plurality of hydrogen sensors are provided on a wafer, such as by using the process shown in Table 1, as shown in 702. In 704, a hydrogen-permeable coating is applied to the wafer. The wafer is then separated into a plurality of dies, as shown in 706. The method may further include providing a temperature sensor and a temperature controller, according to an embodiment of the invention. In another, more basic embodiment, the method consists merely of applying a hydrogen-permeable coating over at least one hydrogen-sensing element disposed on a wafer. Each of these embodiments may be modified and/or refined by using the processes and/or materials described with reference to FIGS. 5A–6B.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams.

The claims should not be read as limited to the described order or elements unless stated to that effect. In addition, use of the term "means" in any claim is intended to invoke 35 U.S.C. §112, paragraph 6, and any claim without the word "means" is not so intended. Therefore, all embodiments that come within the scope and spirit of the following claims and equivalents thereto are claimed as the invention.

What is claimed:

1. A semiconductor wafer including a plurality of hydrogen sensors, said wafer comprising a hydrogen-permeable organic polymer coating disposed over the plurality of hydrogen sensors.

2. The semiconductor wafer of claim 1, further comprising:
   a silicon base portion; and
   a hydrogen sensing portion disposed on the base portion.

3. The semiconductor wafer of claim 1, wherein each of the plurality of hydrogen sensors comprises at least one hydrogen-sensing element.

4. The semiconductor wafer of claim 3, wherein the at least one hydrogen-sensing element includes at least one palladium nickel sensing element.

5. The semiconductor wafer of claim 3, wherein the at least one hydrogen-sensing clement includes at least one sensing element selected from the group consisting of a palladium silicide sensing element and a polymeric sensing element.

6. The semiconductor wafer of claim 3, wherein the at least one hydrogen-sensing element includes at least one sensing element composed of an alloy that resists formation of a hydride phase of a caitalytic metal contained in the alloy.

7. The semiconductor wafer of claim 3, wherein the at least one hydrogen-sensing element includes at least one sensing element selected from the group consisting of a sense resistor, a sense transistor, and a sense capacitor.

8. The semiconductor wafer of claim 3, wherein the at least one hydrogen-sensing element comprises:
   at least one palladium nickel sense resistor for determining hydrogen concentration within a first range; and
   at least one palladium nickel sense transistor for determining hydrogen concentration within a second range.

9. The semiconductor wafer of claim 8, further comprising:
   a temperature sensor for determining a sensor temperature; and
   a temperature controller for controlling the temperature of the sensor.

10. The semiconductor wafer of claim 8, wherein the hydrogen-permeable coating is an organic spin-on polymer.

11. A robust hydrogen sensor, comprising in combination:
    a silicon base portion;
    at least one hydrogen-sensing element disposed on the silicon base portion; and
    a hydrogen-permeable organic polymer coating disposed over the at least one hydrogen-sensing element.

12. The robust hydrogen sensor of claim 11, wherein the at least one hydrogen-sensing element comprises:
    at least one palladium nickel sense resistor for determining hydrogen concentration within a first range; and
    at least one palladium nickel sense transistor for determining hydrogen concentration within a second range.

13. The robust hydrogen sensor of claim 13, wherein the hydrogen-permeable organic polymer coating is an organic spin-on polymer.

* * * * *